United States Patent [19]

Michaels et al.

[11] Patent Number: 5,314,917
[45] Date of Patent: May 24, 1994

[54] METHOD FOR INACTIVATING ENVELOPED VIRUSES AND SPERM

[75] Inventors: Edwin B. Michaels, Milford, Conn.; Daniel Malamud, Merion, Pa.

[73] Assignee: E. B. Michaels Research Associates, Inc., Milford, Conn.

[21] Appl. No.: 673,784

[22] Filed: Mar. 22, 1991

[51] Int. Cl.$^5$ .................. A61K 31/205; A61K 31/13
[52] U.S. Cl. ................................ 514/556; 514/644; 514/843; 514/934
[58] Field of Search ............... 514/556, 644, 843, 934

[56] References Cited

U.S. PATENT DOCUMENTS

| | | | |
|---|---|---|---|
| 4,062,976 | 1/1977 | Michaels | 424/319 |
| 4,075,350 | 2/1978 | Michaels | 424/316 |
| 4,107,328 | 8/1978 | Michaels | 424/316 |
| 4,145,436 | 3/1979 | Michaels | 424/325 |
| 4,183,952 | 1/1980 | Michaels | 424/316 |
| 4,839,158 | 6/1989 | Michaels | 424/54 |

OTHER PUBLICATIONS

Chemical Abstract 111: 99431m (1989).
Chemical Abstracts 115: 150372e (1991).
Bowers, B. "A Biotech Worker Pursues the Formula for Success" Wall Street Journal, Jan. 30, 1991.
A-M Corner, et al., "Anti-Viral Activity of C31G" VII International Conference of AIDS, Florence, Italy, Jun. 16-21, 1991 Stn. accession no. 91:446745.
A. M. Corner et al., Journal of Clinical Dentistry 2(2):34–38 (1990).
A. M. Corner, et al., Antimicrobial Agents and Chemotherapy 32(3):350–353 (1988).
Chemical Abstract 100(15):116324w (1984).
Chemical Abstract 99(13):98853x (1983).

Primary Examiner—Frederick E. Waddell
Assistant Examiner—T. J. Criares
Attorney, Agent, or Firm—Ladas & Parry

[57] ABSTRACT

There is provided methods for inhibiting the activity of enveloped viruses, treatment of viral infections and method inactiviting sperm. There is provided articles for use in these methods.

32 Claims, 9 Drawing Sheets

INACTIVATION OF HIV BY C31G OR N-9

| CONCENTRATION (%) | P24 % REDUCTION | |
|---|---|---|
| | C31G | N-9 |
| .006 | 0 | 0 |
| .012 | 20 | 85 |
| .025 | 99 | 98 |
| .050 | 99 | 98 |
| .100 | 95 | 97 |
| .200 | 100 | 100 |

FIG. 9

METHOD FOR INACTIVATING ENVELOPED VIRUSES AND SPERM

BACKGROUND OF THE INVENTION

1. Field of the Invention

The present invention relates to a novel method and novel articles for inhibiting the activity of enveloped viruses. The invention also relates to treatment of viral infections. More particularly, the invention relates to a method for inhibiting the development of diseases and infections caused by enveloped viruses. In one aspect the invention particularly relates to a method of inhibiting the activity viruses whose major mode of transmission is sexual. In other aspects the invention also relates to methods of inhibiting the activity of enveloped viruses whose mode of transmission is nonsexual. The compositions of use in the invention are also effective in the inhibition of bacteria and fungi which coexist with viruses or viral infections. Additionally, the invention relates to a treatment for virus related diseases, particularly sexually transmitted diseases related to AIDS, and to diseases related to this and other opportunistic infections of the immune-compromised host.

The method of the invention relates to using mixtures of betaines and amine oxides in the inhibition of viruses and treatment of viral infections. The betaine is selected from the group consisting of (a) an alkyl-N-betaine, an alkyl-N-sulfobetaine, an acyl-N-betaine, an alkyl N-substituted aminopropionic acid and an alkylimidazolinium betaine and the amine oxide is selected from the group consisting of (b) an alkyl-N, N-dimethylamine oxide, an alkyl-N, N-dihydroxyethylamine oxide and an acylamide t-amide oxide. The term "betaine" when used herein means an N-dimethyl glycine and their lower alkyl homologs. The term includes N-dimethyl amino propionic acids and sulfo betaines which are the sulfonic acid analogs of such compounds. Unless otherwise specified a N-dimethyl compound is intended. More particularly, the invention relates to a method for employing mixtures of alkyl N-di (lower alkyl) betaines and alkyl N-di (lower alkyl) amine oxides in the inhibition of enveloped viruses and use of these mixtures in the treatment of infections caused by these viruses.

The mixtures may also be used as spermicides, either alone or in combination with conventional spermicides. These mixtures may be used in combination with contraceptive devices or may be incorporated into the contraceptive device.

2. Description of the Prior Art

It is known that certain mixtures of amines are effective antimicrobial agents against gram negative and gram positive bacteria. For instance, it is known that certain mixtures of a) alkyl-N-betaine, alkyl-N-sulfobetaine, acyl-N-betaine, alkyl N-substituted aminopropionic acid or an alkylimidazolinium betaine and (b) alkyl-N, N-dimethylamine oxide, alkyl-N, N-dihydroxyethylamine oxide or acylamide t-amide oxide can be used for skin degerming, cleansing and deodorizing (see for example U.S. Pat. No. 4,183,952, issued to E. B. Michaels; U.S. Pat. No. 4,075,350 issued to E. B. Michaels, and U.S. Pat. No. 4,107,328; issued to E. B. Michaels). These compositions are also useful for long term inhibition of body odor. Mixtures of the same active ingredients are also known to enhance oral hygiene by reducing oral microflora and inhibiting formation of dental plaque. (U.S. Pat. No. 4,839,158 issued to E. B. Michaels). Compositions of this type are also known to be effective fungicides. Corner, A. M., et al. *Antimicrobial Agents and Chemotherapy*, 32(3):350-353 (March 1988); Corner, A. M. *The Journal of Clinical Dentistry*, Vol. 2(2): 34-38. (1990)). (See also U.S. Pat. Nos. 4,075,350, 4,107,328, 4,183,952 and 4,839,158 issued to E. B. Michaels.)

It is also known that nonionic surface-active agents possessing ether or amide linkages between the hydrophilic and hydrophobic portions of the molecule rapidly inactivate the infectivity of herpes simplex virus I and II. (Asculai, S. S., et al. *Antimicrobial Agents Chemotherapy*. Vol. 13:686-690 (1978)). Asculai et al. also states that cytocidal activity has been used as an index of antiviral activity. The compositions utilized in this invention have an advantage over the compositions described in Asculai et al. in that these compositions inactivate viruses and bacteria while exhibiting low cytocidal activity.

The spermicide Nonoxynol-9 (N-9), has been found to have bactericidal and viricidal effects. For example, N-9 has been found to inactivate viruses related to AIDS (e.g. HIV, human immunodeficiency virus) and herpes simplex viruses (HSV I and II). In vitro, N-9 has been shown to be effective against the organisms that cause gonorrhea, chlamydia, syphilis, trichomoniasis, and other sexually transmitted diseases. (U.S. Pharmacopeial Convention USPDI Update 1990 pps. 755-756).

SUMMARY OF THE INVENTION

It has now unexpectedly been found that certain hereinbelow defined mixtures of betaines such as (a) alkyl-N-betaines, alkyl-N-sulfobetaines, acyl-N-betaines, alkyl-N-substituted aminopropionic acids and alkylimidazolinium betaines, and amine oxides such as (b) alkyl-N, N-dimethylamine oxides, alkyl-N, N-dihydroxyethylamine oxides or acylamide t-amide oxides in acceptable diluents, carriers and excipients are effective in inhibiting the activity of enveloped viruses. The invention provides a method of inhibiting the activity of enveloped viruses for which a major mode of transmission is sexual. The invention relates to a method for treating diseases and infections caused by enveloped viruses. These compositions are also effective in the inhibition of bacteria and fungi that co-exist with viruses or viral infections and for treatment of bacterial and fungal infections which co-exist with viruses or viral infections. The invention also provides a method for disinfecting air and surfaces contaminated with enveloped viruses.

The invention also provides a method for preventing the transmission of enveloped viruses.

The compositions used in the method of the present invention can also be used as spermicides. These compositions can be used alone, with other known spermicides and with or incorporated into contraceptive devices such as condoms, sponges, vaginal inserts, contraceptive films, diaphragms, suppositories, contraceptive patches or sustained release devices. These compositions can also be incorporated into douches. The compositions can be incorporated into wipes. For use as viricides, these compositions can be applied alone; with other spermicides; and with or incorporated into the contraceptive devices described above.

The compositions can also be applied in the form of a foam, gel, cream, salve, jelly or lotion. The compositions can also be applied in the form of a liquid, aerosol, mist or spray.

DETAILED DESCRIPTION OF THE INVENTION

The method of the invention relates to using mixtures of betaines and amine oxides in the inhibition of enveloped viruses and treatment of viral infections caused by enveloped viruses. The method of the invention also relates to using mixtures of betaines and amine oxides in the inactivation of enveloped viruses. The betaines that can be used in this invention are alkyl-N-betaines, alkyl-N-sulfobetaines, acyl-N-betaines, alkyl N-substituted aminopropionic acids or alkylimidazolinium betaines or mixtures thereof. The amine oxides that can be used in this invention are alkyl-N, N-dimethylamine oxides, alkyl-N, N-dihydroxyethylamine oxides or acylamide t-amide oxides or mixtures thereof. These compositions are also effective for the treatment of viral, fungal, and microbial infections and contaminations. These compositions are effective in inhibiting enveloped viruses that are transmitted sexually or nonsexually. These compositions are also effective in the inhibition of bacteria and fungi which coexist with viruses or viral infections. These compositions can also be used topically.

Typically, these compositions are applied to areas where viruses are or can be transmitted. This includes application in the vagina, to mucous membranes, and to the skin.

These compositions can also be used as spermicides, either alone or in combination with other spermicides. These compositions can also be used with or incorporated into contraceptive devices such as, for example, condoms, diaphragms, sponges, contraceptive films, suppositories, sustained release devices, and contraceptive patches. For example, the composition may be incorporated into a lubricant applied to a condom or as part of a reservoir at the tip of a condom, or incorporated into a contraceptive sponge, contraceptive film, suppository, sustained release device or contraceptive patch. A contraceptive film can comprise the composition described above, together with, Type A gelatin, cellulose gum and a polyhydric alcohol. The compositions can also be used in contraceptive foams, gels, jellys, creams. The compositions can also be used in douches.

For use in preventing the transmission of viruses, these compositions can be used alone, with other spermicides and with or incorporated into a contraceptive device as described above. This invention also comprises a method for inhibiting the transmission of viruses that cause sexually transmitted diseases which comprises applying the compositions to those parts of the anatomy that are exposed to body fluids emanating from another during sexual activity.

Figure 4:
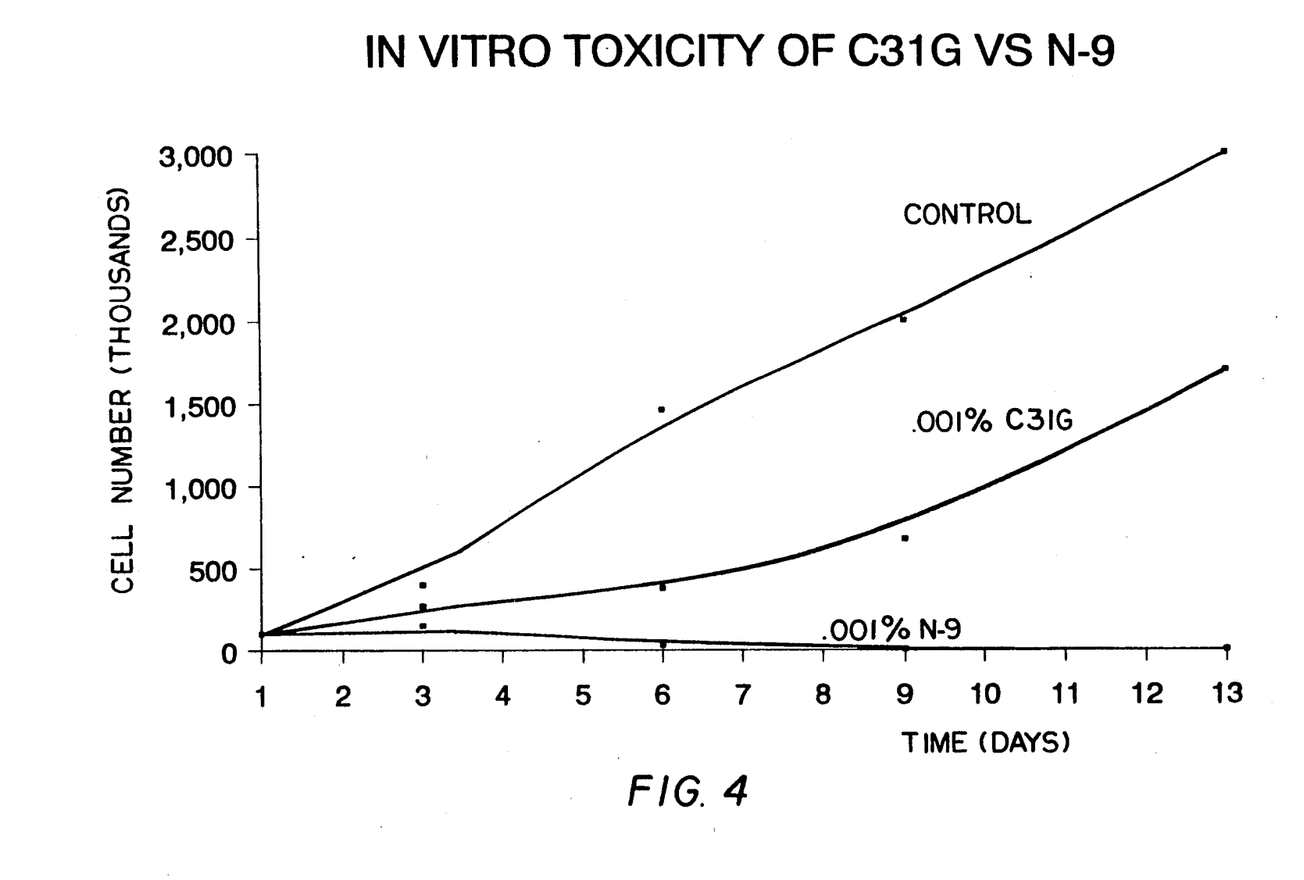
FIG. 4: is a graph showing in vitro toxicity of C31G vs. N-9 on sup-TI cells.
Figure 5:
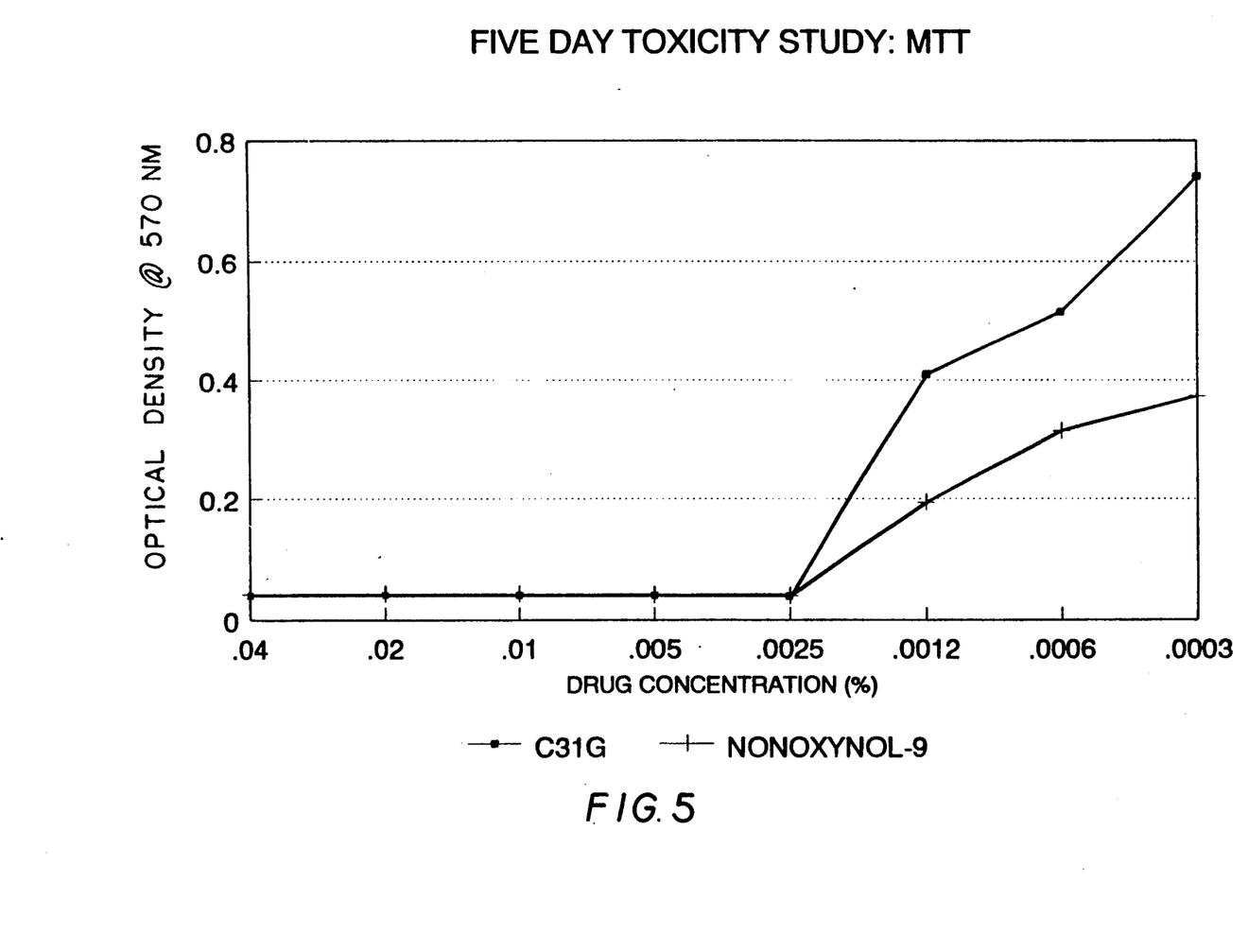
FIG. 5: is a graph showing a five day toxicity study of C31G vs. N-9 on CEM cells.

These compositions have also unexpectedly been found to be less toxic to mammalian cells than Nonoxynol-9 (N-9) (See FIGS. 4 and 5). Table 1 shows that these compositions have equivalent spermicidal activity to N-9, which is one of the few surfactants approved by the FDA for use as a spermicide.

For use in topical applications, the compositions can also be incorporated into liquids, creams, salves, lotions, foams and gels.

The invention also provides a method for disinfecting air and inanimate surfaces, for example, in an operating room or laboratory. More particularly, this invention provides a method for disinfecting areas which are contaminated with enveloped viruses. These compositions can also be incorporated into sprays, mists, wipes, aerosols or devices which produce sprays, mists or aerosols. These compositions can also be applied as liquids.

According to the method of this invention, these compositions may be used as viricides, fungicides and bactericides.

The compositions employed in the method of the invention comprise an admixture of betaines and amine oxides. The betaines used in this invention are selected from the group consisting of (a) alkyl-N-betaines, alkyl-N-sulfobetaines, acyl-N-betaines, alkyl N-substituted aminopropionic acid, alkylimidazolinium betaines and mixtures of two or more thereof. Typically the betaines have two lower alkyl groups bonded to the nitrogen atom. Most effectively they have two methyl subsstituts on the nitrogen atom. The amine oxides used in this invention are selected from the group consisting of b) a an alkyl-N,N-dimethylamine oxides, alkyl-N,N-dihydroxyethylamine oxide or acylamide t-amine oxides and mixtures of two or more thereof. Typically, the betaine and amine oxide components are present in a molar ratio of from 1:5 to 5:1, preferably in a molar ratio of 1:1. The alkyl-N-betaine, the alkyl-N-sulfobetaine, the acyl-N-betaine, the alkyl N-substituted 2-aminopropionic acid and alkylimidazolinium betaine (also referred to as cocoamphoacetates) employed as the components (a) of the composition of the invention have structures, respectively, as follows:

RNHCH₂CH₂COOH or RN(CH₂CH₂COOH)₂ where R is a higher alkyl group having from 10 to 18 carbon atoms, preferably from 12–16 carbon atoms.

When used herein the term lower alkyl means an alkyl group of from 1 to 3 carbon atoms Illustrative of these aforementioned substances are: (1) coco-N-betaine, cetyl-N-betaine, stearyl-N-betaine, isostearyl-N-betaine, oleyl-N-betaine; (2) coco-N-sulphobetaine, cetyl-N-sulphobetaine, stearyl-N-sulfobetaine, isostearyl-N-sulfobetaine, oleyl-N-sulfobetaine; (3) cocoamido-N-betaine, cetylamido-N-betaine, stearylamido-N-betaine, isostearylamido-N-betaine, oleylamino-N-betaine; (4) N-coco-2 aminopropionic acid, N-cetyl-2-aminopropionic acid, N-stearyl-2-aminopropionic acid, N-isostearyl-2-aminopropionic acid, N-oleyl-2-aminopropionic acid, N-stearylbis (2-aminopropionic acid), N-oleyl-bis (2-aminopropionic acid), N-coco-bis (2-aminopropionic acid), N-cetyl-bis (2-aminopropionic acid), (5) N-lauryl-bis (2-aminopropionic acid) 1-hydroxyethyl-1-carboxymethyl-2-decylimidazolium betaine; 1-hydroxyethyl-1-carboxymethyl-2-dodecylimidazolium betaine; 1-hydroxyethyl-1-carboxymethyl-2-cocoimidazolium betaine; 1-hydroxyethyl-1- 1-carboxymethyl-2-stearylimidazolium betaine; 1-hydroxyethyl-1-carboxymethyl-2-oleylimidazolium betaine; or mixtures of the same.

When used here the term "coco" is that used in the CTFA (designations of Cosmetic and Toiletry and Fragrance Association, Wash., D.C.) and is used to indicate alkyl groups present in coconut oil, i.e. a mixture of alkyl groups of from 10 to 18 carbon atoms. The designations of the compounds listed herein are those of the CTFA.

The (1) alkyl-N,N-diethylamine oxide, (2) alkyl-N,N-dihydroxylethylamine oxide, or (3) acylamide t-amine oxide employed as component (b) of the aforementioned mixture, respectively, have the structure:

where R is a higher alkyl group of from 10 to 18 carbon atoms, for instance, radicals such as decyl, undecyl, lauryl, tridecyl, myristyl, cetyl, stearyl, isostearyl or oleyl. Exemplary of the amine oxides are: decyl-N,N-dimethylamine oxide, lauryl-N,N-dimethylamine oxide, stearly-N-N-dimethylamine oxide, oleyl-N,N-dimethylamine oxide, coco-N,N dihydroxyethylamine oxide, cetyl-N,N-dihydroxyethylamine oxide, oleyl-N,N-dihydroxyethyl-amine oxide, N,N-dihydroxyethyla-mine oxide, oleyl-N,-N-dihydroxyethyl-amine oxide and mixtures of the same.

The components (a) and (b) are usually admixed and acid is then added in an amount necessary to adjust the pH of a 0.5% solution to between 4–8, preferably to pH 4.5–5.5. The pH of an aqueous solution comprising the above enumerated components of the invention is determined by employing an aqueous solution of 0.5%, by weight, total of active components typically at a glass electrode, to precisely define the acidity of the composition.

In general, the acid used to adjust the overall composition to the required pH is any organic or inorganic acid that is compatible with the intended use of the composition, for example, hydrochloric acid, phosphoric acid, sulfuric acid, citric acid, acetic acid or nicotinic acid.

The balance of the composition, after allowing for the acid is usually an acceptable solvent, such as water or a lower ($C_1$–$C_4$) monohydric aliphatic alcohol, for a total of 100 parts or more. Where water is employed, small amounts of a lower alkyl alcohol, such as ethanol or propanol, may also be added to provide ease in formulation. Acceptable diluents, carriers and excipients are, for example, ethyl or isopropyl alcohols, polyethylene glycol, povidone, polyhydric alcohols, glycerine, cellulose gums, gelatin, colorants and fragrances. If necessary, the pH of the total composition is then adjusted to the requisite pH by adding a suitable inorganic or organic acid thereto.

The result is a substantially uniform, homogeneous, relatively nontoxic composition having enhanced activity against enveloped viruses, bacteria and fungi.

It has been unexpectedly found that these compositions exhibit (1) low mammalian cell toxicity, a property which is known to correlate with low irritation and low toxicity when used in contact with mucous membranes (*Journal Clinical Dentistry* 2(2):34–38, (1990)), and (2) highly efficacious inactivation of enveloped viruses although cytocidal activity is low. In the past, research has used cytocidal activity as an index of activity. (Asculai, S. S., Antimicrb. Agents Chemother. 13:678–690 (1978))

In practice, the total amount of the components (a) and (b) of the overall composition can range from 0.01%–40%, preferably from 0.03%–30% depending on the intended means of use. For example, concentrations used are, approximately 20%–30% in contraceptive films and 0.2% to 2% in gels.

Compositions for use in this invention comprise alkyl N-di (lower alkyl) glycines and alkyl N-di (lower alkyl) amine oxides, wherein the lower alkyl is $C_1$–$C_3$. One class of betaines I have found to be partically useful in this invention are the alkyl N-dimethyl betaines, such as cocobetaines and lauryl betaines. Particularly useful amine oxides for use in this invention are the an alkyl N-dimethyl amine oxides, such as cocodimethyl amine oxides and lauryl dimethyl amine oxides.

One particular composition that can be used in this invention comprises cocobetaine, cocamine oxide and citric acid monohydrate.

Another composition that can be used in this invention comprises lauryl betaine, lauramine oxide and citric acid monohydrate.

In such compositions, the molar ratio of betaines to amine oxides is normally from 5:1 to 1:5, preferably in a molar ratio of 2:1 to 1:2, more preferably about 1:1.

Other compositions that can be used in this invention comprise mixtures of betaines, amine oxides, gelatin having a Bloom strength of 100–300 and a molecular weight from about 75,000 to about 300,000, polyhydric alcohols and cellulose gums. Such compositions are described in a copending U.S. application being filed simultaneously with the present application and having attorney docket no. U8186.

Compositions used in this invention can inhibit the activity of viruses that are related to AIDS. It is also expected that these compositions can inhibit the activity of HSV-1 and HSV-2. It is also expected that the compositions used in this invention can inhibit Hepatitis A, B and C. It is expected that the compositions can be used to inhibit viruses, bacteria and fungi which are associated with sexually transmitted diseases (STD's).

The compositions of this invention may be useful in relation to the following:

1) Transmission of HIV is often associated with the cotransmission of other viral and/or microbial pathogens. Indeed, some investigators have suggested that HIV may not be the sole agent responsible for AIDS (see Duesberg, P. H. (1991) *Proc. Natl. Acad. Sci.* 88:1575–1579; Lemaitre, M., Guetard, D., Henin, Y., Montagnier, L. and Zerial, A.(1990). *Res. Virol.* 141:5–16). For this reason, antimicrobial agents, such as those described in this application, with a broad spectrum of activities against viruses, bacteria, and yeasts such as Candida may be of particular value in the prevention and treatment of Acquired Immune Deficiency Syndrome (AIDS).

2) It is thought that certain bacteria known to cause STD's may aid in HIV transmission. In persons who have been exposed to HIV, certain bacteria which cause STD's often fail to respond to therapies that are otherwise highly effective. HIV infection may help the spread of a bacterial STD that in turn helps to spread HIV. STD's such as chlamydia, chancroid, syphilis, genital herpes and gonorrhea which cause ulcerations of the genital skin seem to increase the risk of acquiring or transmitting HIV infection sexually. Aral, S. O., et al. *Scientific American,* 264(2):62–69 (February 1991).

The compositions described above may also be of use to inactivate other enveloped viruses, including vaccinia, varicella, herpes zoster, cytomegalovirus, Epstein Barr virus, influenza, mumps, measles, rhinovirus, rabies and rubella. In order to facilitate a further understanding of the invention, the following examples are presented primarily for the purposes of illustrating more specific details thereof. The invention is not to be deemed as limited thereby except as defined in the claims.

EXAMPLE 1

The composition described below is a concentrate of C31G, an equimolar preparation of cocobetaine and cocodimethylamine oxides (designations of CTFA Cosmetic and Toiletry and Fragrance Association, Wash., D.C.) [CFTA] which can be used in a number of different configurations.

Cocobetaine; 31.5% active ingredient (AI): 405.5 lb,
Cocamine oxide, 31.5% (AI): 325 lb,
Citric acid monohydrate, USP: 26 lb,
Purified water, USP: 26 lb, To make about 782.5 lb C31G at 29.6% AI, at a dilution 1% AI; pH=4.9.

EXAMPLE 2

The spermicidal activity of C31G of example 1 was compared to the spermicidal activity of nonoxynol-9 (N-9).

Figure 1:
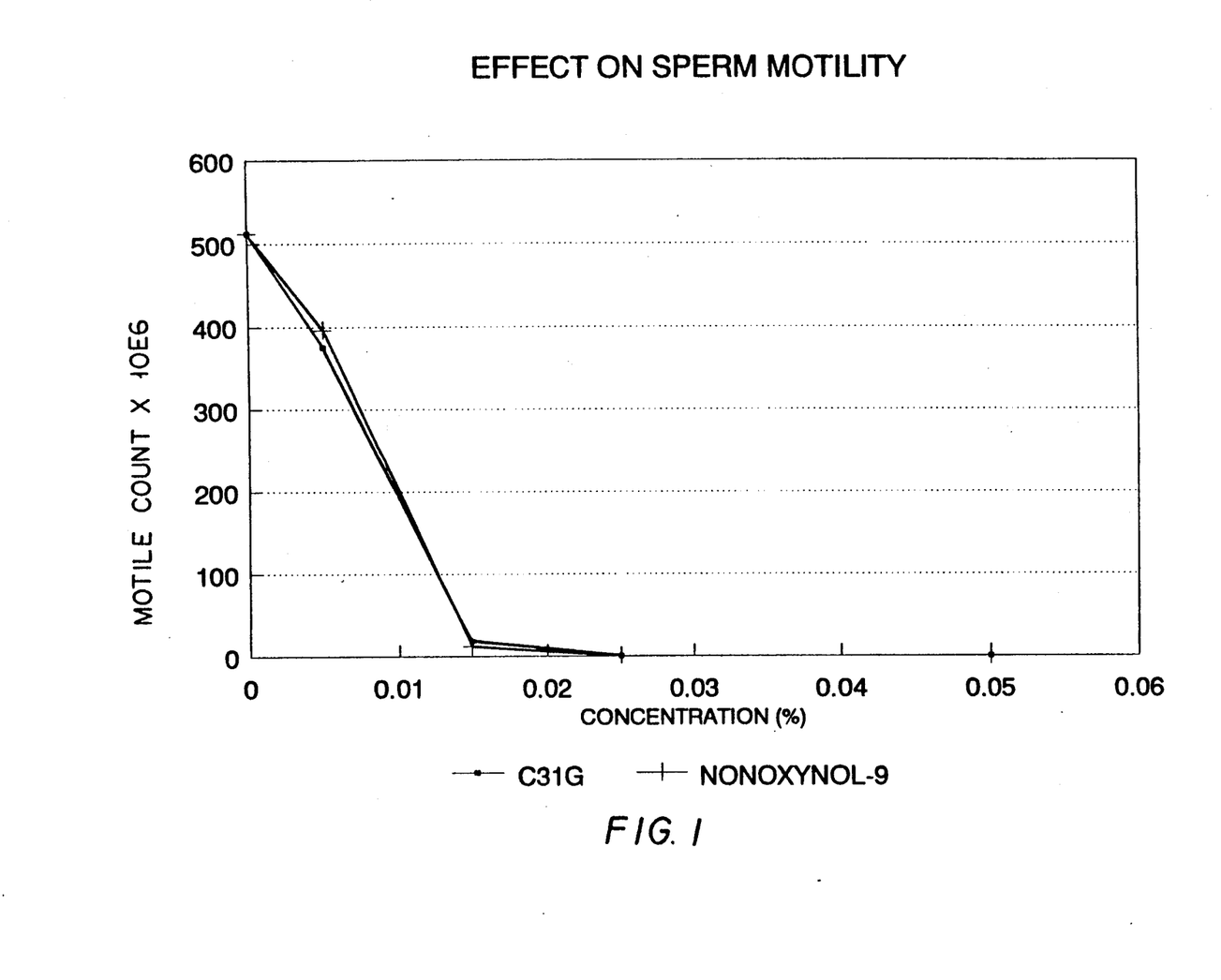
FIG. 1: is a graph showing the effect of C31G (a composition according to the present invention) and the effect of Nonoxynol-9 (N-9) on sperm motility.
Figure 2:
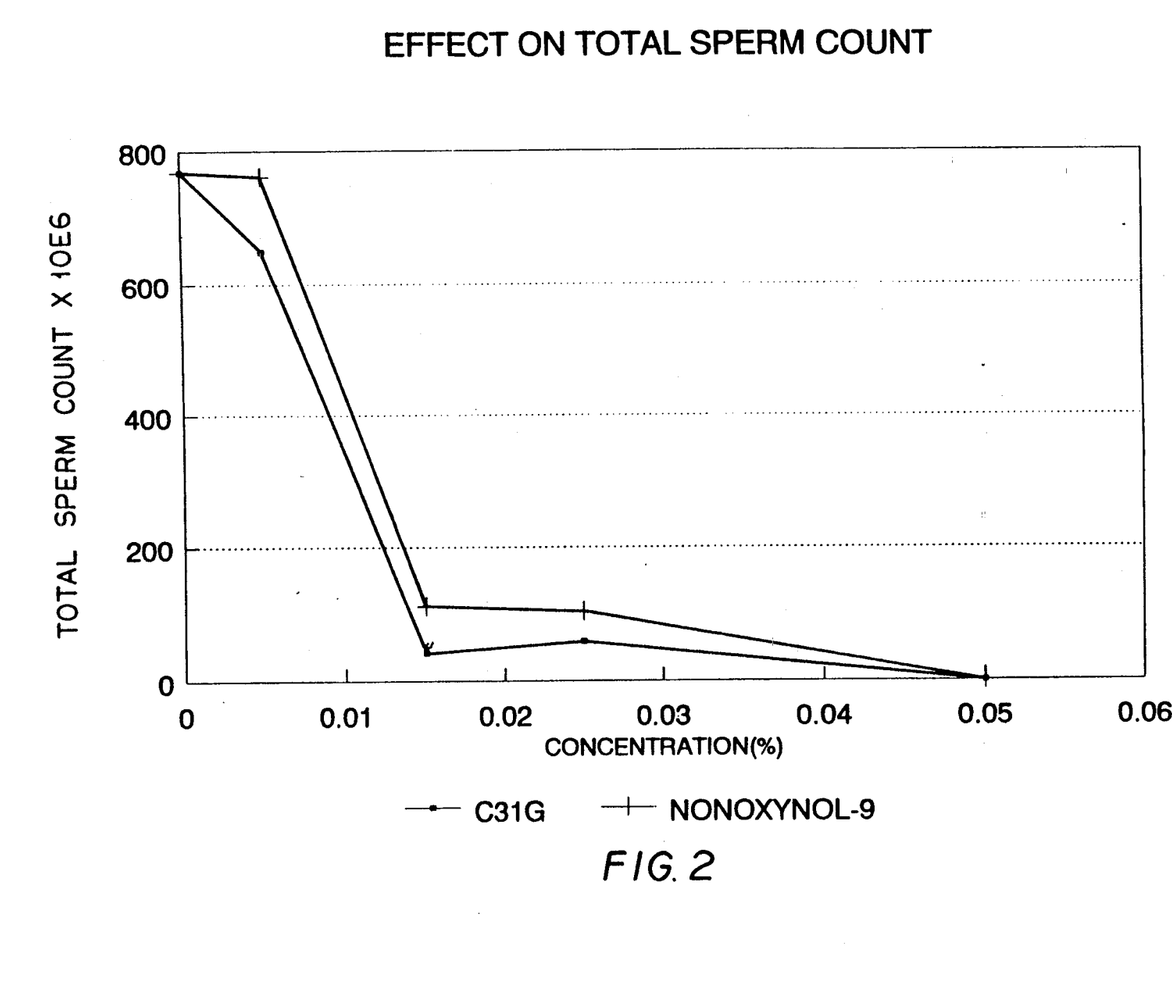
FIG. 2: is a graph showing the effect of C31G and the effect of Nonoxoynol-9 (N-9) on total sperm count.
Figure 3:
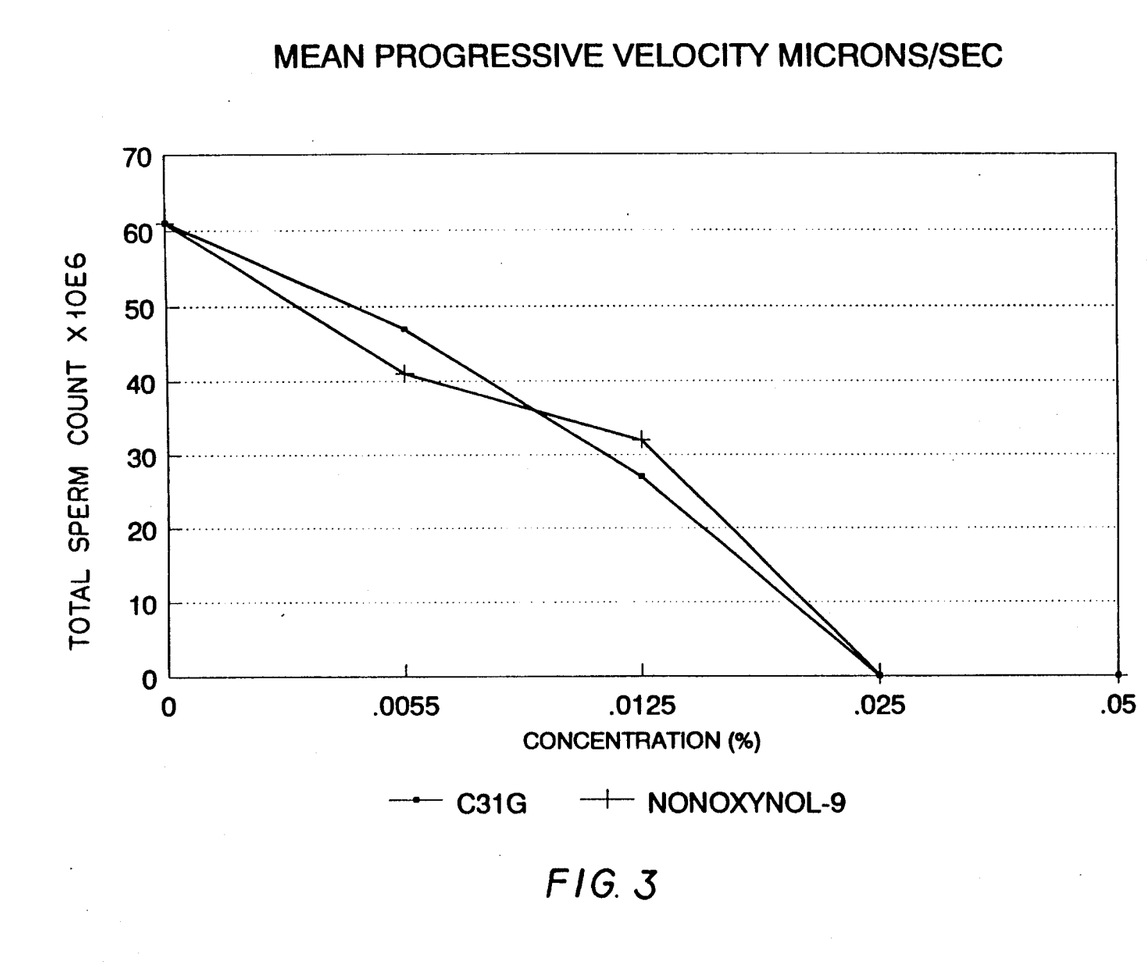
FIG. 3: is a graph showing the effect of C31G and the effect of Nonoxoynol(N-9) on the mean progressive velocity of sperm.

The studies were conducted using the Hamilton-Thorn Sperm Motility Analyzer. Samples of pooled washed semen were incubated with dilutions of the two compounds for fifteen seconds and were analyzed (in triplicate) for determination of the minimum concentration for inactivation by the following criteria:

1. Inhibition of sperm motility (FIG. 1)
2. Decrease in total sperm count (FIG. 2)
3. Inhibition of the mean progressive sperm velocity (FIG. 3)

As shown in Table 1, C31G and N-9 gave identical results:

TABLE 1

| Minimum Concentration for Spermicidal Activity | | |
|---|---|---|
| | C31G | N-9 |
| Total Inhibition of Motility | 150 ppm | 150 ppm |
| 90% Decrease in Sperm Count | 150 ppm | 150 ppm |
| 50% Decrease in Progressive Velocity | 125 ppm | 125 ppm |

EXAMPLE 3

The cytotoxic effects of C31G and N-9 on mammalian cells were determined in several types of assays. Cell toxicity is an indication of the relative safety and comfort in use of surfactants in contraceptives or prophylactics.

As shown in FIG. 4, a two week study monitoring drug effects on SUP-TI cells, (a human lymphocytic cell line), C31G demonstrated minimal toxicity at 0.001% [10 ppm] while N-9 at the same concentration was extremely toxic.

EXAMPLE 4

FIG. 5 shows MMT reduction in CEM cells after five days of continuous exposure. Under these conditions C31G showed no toxicity to mammalian cells at 3 ppm [0.0003%] while N-9 showing toxicity, reducing mammalian cell viability by 50% at the same concentration. It is unexpected that a compound having the same spermicidal activity as N-9 would be less toxic to mammalian cells than N-9.

EXAMPLE 5

Antiviral activity of C31G was tested using HSV-1 and HIV-1.

To test the effect of C31G and N-9 on herpes simplex virus type-1 (KOS strain), the virus stock was prepared in Vero (African green monkey kidney) cells. The virus was released from the cells by one freeze-thaw cycle followed by sonication. The virus titer was $4.5 \times 10^8$ plaque forming units (PFU)/ml, as determined on Vero cells. The drug formulations used were identical to the drugs in the spermicidal study.

The stock concentration of each drug was 5%. Two-fold serial dilutions were made, down to 0.04%, in PBS pH 7.4 at room temperature. 24 ul of each dilution was added to 220 ul of virus ($10^8$ PFU), giving final concentrations of 0.5-0.004%. These samples were incubated at room temperature for 10 min, and then 100 ul of each was immediately diluted to 1 ml with ice-cold DMEM/5% FBS. 10-fold serial dilutions were then made, down to $10^{-7}$, for titration of remaining infectious virus on Vero cells in 24-well plates. Plaques were counted 36 hours post-infection.

TABLE 2

| Concentration (%) | Residual Virus (PFU/ml) | |
|---|---|---|
| | N-9 | C31G |
| 0.004 | $3.5 \times 10^8$ | $3.5 \times 10^8$ |
| 0.008 | $2.7 \times 10^8$ | $3.3 \times 10^8$ |
| 0.015 | $1.1 \times 10^8$ | $2.5 \times 10^5$ |
| 0.03 | 3200 | <167 |
| 0.06 | <167 | <167 |
| 0.13 | <167 | <167 |
| 0.25 | <167 | <167 |
| 0.5 | <167 | <167 |

Note that these are titers (i.e. PFU/ml), rather than absolute numbers of PFU. The titer determined for untreated virus was $4.7 \times 10^8$ PFU/ml in the experiment using N-9 and $4.5 \times 10^8$ PFU/ml in the experiment using C31G.

Figure 6:
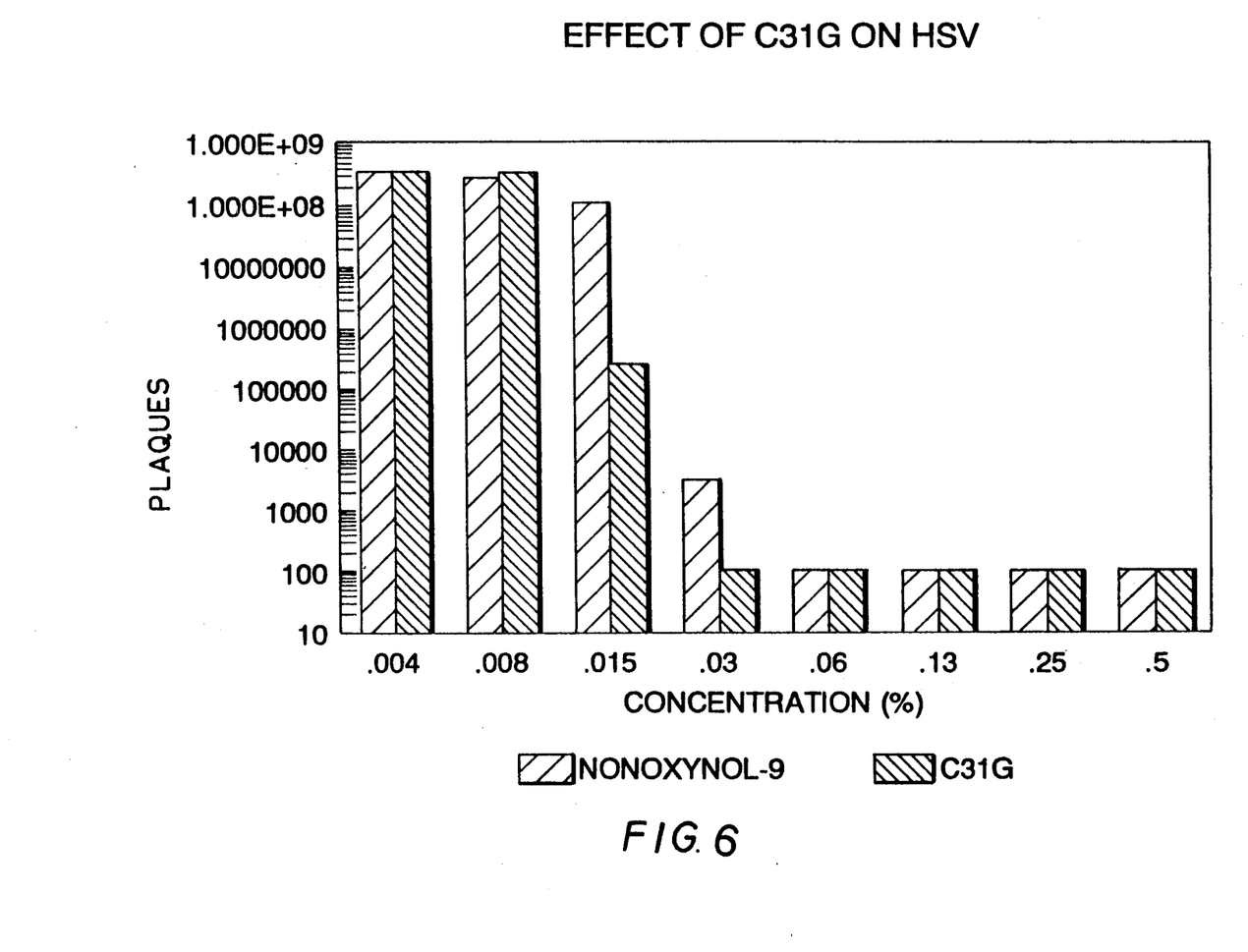
FIG. 6: is a graph showing comparing the effects on C31G vs. N9 on HS

It is noted that complete inhibition of plaque formation by C31G occurs at more than one dilution below that of N-9. See FIG. 6.

EXAMPLE 6

The inactivation of HIV-1 (AIDS) virus was studied in two experiments. The first study compared the effects of C31G of HIV-1 at two different exposure times, 2 minutes and 45 minutes. The next study compared the relative activity of C31G and N-9 on HIV using the same virus strain and measuring antiviral activity by reduction of virus titer as determined by reduction of P-24 HIV antigen.

The protocol and results of the first study follow:

EFFECTS OF C31G ON HUMAN IMMUNODEFICIENCY VIRUS

Materials

Virus: HIV-1 strain 3B ($5 \times 10^5$ ID50 units/ml)
Cells: SUP-T1 cell line (CD4+ lymphoid cells which produce characteristic cell fusion with giant cells and syncytia when infected with HIV)

Protocol

1. Serial fourfold dilutions of C31G in PBS (4.0% –0.004% and PBS alone as control) were prepared. pH was adjusted to 5.5.
2. Pooled aliquots of viral stock were prepared and C31G was added at each concentration, at 1:9 detergent:virus ratio (1:10 detergent dilution). These were incubated for either 2 or 45 minutes.
3. Serial fourfold dilutions of each virus/detergent mixture down to 1:4096 were prepared.
4. 16.6 ul of each virus/detergent dilution from each series were added to four replicate wells of SUP-T1 cells ($10^4$ cells in 150 ul volume; 1:10 detergent dilution followed by further fourfold dilutions).
5. The wells were examined twice weekly for two weeks and each well was scored positive or negative for the presence of characteristic viral syncytia or non-syncytial ghost formation due to detergent lysis.

Notes

Virus was exposed to C31G at a 1:10 dilution of initial concentration for either 2 or 45 minutes, followed by another 1:10 dilution and then serial four-fold dilutions for the entire period.

Figure 7:
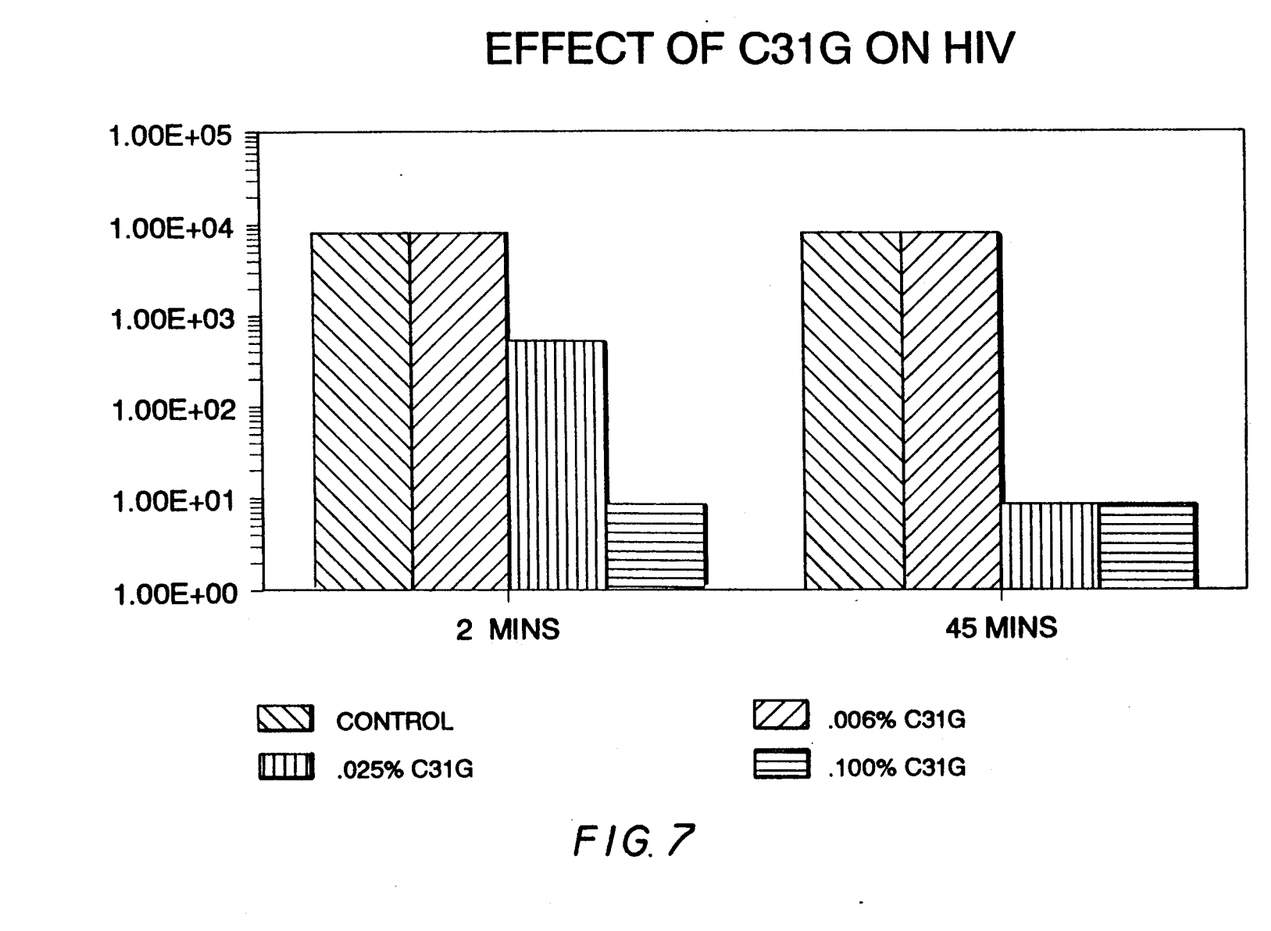
FIG. 7: is a graph showing the effect of C31G on HIV.

Cells were exposed to C31G at a 1:100 and then serial fourfold dilutions of initial concentration for entire period. See FIG. 7.

EXAMPLE 7

The protocol and results of the second study follows:

Materials

Cells: CEM cell line ATCC #119 T cell
Virus: $HIV_{IIIb}$
Test compounds: Compounds C31G and N-9, supplied as 5% solutions, were filtered through a low binding 0.22 filter prior to diluting.

Protocol

Figure 8:
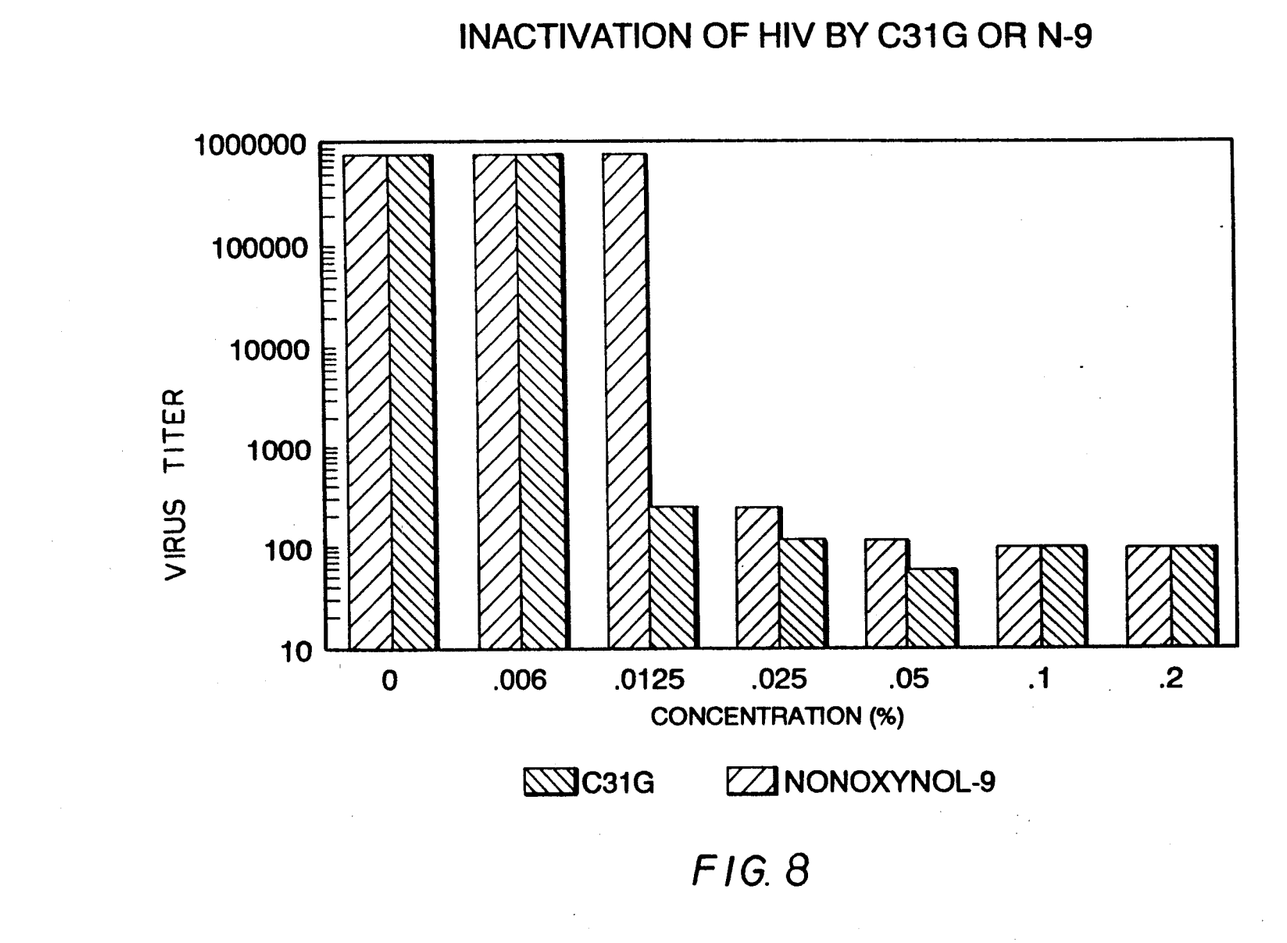
FIG. 8: is a graph comparing inactivation of HIV by C31G and N-9.
Figure 9:
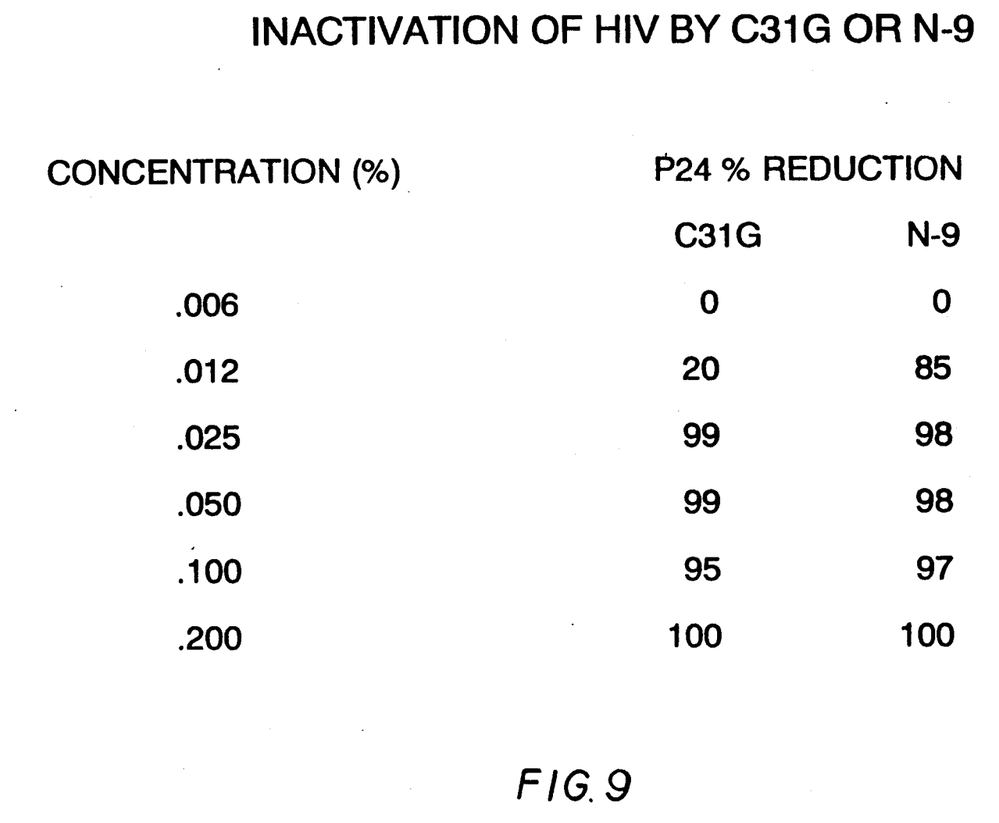
FIG. 9: is a chart comparing inactivation of HIV by C31G and N-9.

1. Serial 2 fold dilutions of compounds N-9 and C31G in PBS adjusted to pH 5.5 were prepared. The highest concentration was 4% and the lowest was 0.03%. The initial concentrations were 4, 2, 1, 0.5, 0.25, 0.125, 0.06, and 0.03%, as well as a control without drug. The control titration was done twice.
2. 14 $12 \times 75$ mm sterile plastic tubes with 0.9 ml each of concentrated virus (at least $1 \times 10^6$ $TCID^{50}$/ml) were set-up. 0.1 ml of each compound dilution were transferred to a tube (dilution of 1:10 of the initial drug concentrations).
3. Incubation was for 10 minutes at room temperature, and was terminated (or slowed) by diluting 1:10 in complete growth medium (on ice).
4. Additional serial 5 fold dilutions (7 dilutions, with the final dilution equal to 1:781250) in complete medium on ice were prepared.
5. 50 ul of the virus dilutions were added to quadruplicate wells of 96 well trays (U bottom) containing $3 \times 10^4$ CEM cells in 50 ul.
6. 60 minutes were allowed for virus absorption. The cells were washed twice by centrifuging the plates at 1500 rpm for 5 minutes and aspirating the supernatents. The final cell pellets were resuspended in 100 ul of medium and transferred to flat bottom 96 well trays. The results are shown in FIGS. 8 and 9.

EXAMPLE 8

Formulations for Contraceptive/AntiInfective Preparations

Concentrate {CCon} comprises:

| | |
|---|---|
| Lauryl Betaine (30% ai) | 1000 pts |
| Lauramine Oxide (30% ai) | 870 pts |
| Citric Acid monohydrate | 69 pts |

The above are stirred to a uniform solution. At a dilution of one part to 30, the composition should have a pH of 4.85 at the glass electrode. Putative concentration equal to 28.5% active ingredients (ai).

EXAMPLE 9

Suppositories (inserts) for use with or without Condoms

| | |
|---|---|
| CCon (of Example 8) | 526 pts |
| PEG-32 | 4000 pts |
| PEG-20 | 1000 pts |
| Povidone | 74 pts |

The above are stirred to solution at 45° C. and injected into molds, cooled and ejected for packaging.

EXAMPLE 10

Contraceptive Sponge

| | |
|---|---|
| CCon (of Example 8) | 3.5 gms |

Added to each mold for curing urethane. Charge in mold provided with polyester loop for post coital removal of the sponge.

EXAMPLE 11

Spermicidal Gels, Creams or Jellies for use with Cervical Caps Condoms, Diaphragms or alone prior to coitus.

| | | |
|---|---|---|
| Gel-1 | CCon (of Example 8) | 7.0 pts |
| | Gelatin A200 | 1.5 pts |
| | Glycerine | 10.0 pts |
| | Hydroxyethyl Cellulose (high viscosity Grade) | 0.4 pts |
| | Water | 81.1 pts |
| Gel-2 | As above with the substitution of 1.0 pt of Nonoxynol-9 for 3.5 pts of CCon (of Example 8). | |

Procedure—The gelating and cellulose gum are triturated in the glycerine and added to the water at 45° C. and stirred to solution. The surfactants are added to the vessel and the warm solution removed for packaging. A uniform fluid high viscosity gel forms on cooling.

Jelly 1 and 2

Clear fluid contraceptive jellies are prepared by substitution of 1.5 pts of high viscosity grade hydroxypropyl or hydroxypropylmethyl cellulose for the gelatin and hydroxyethyl cellulose of the above examples.

Creme 1 and 2

The Gel formulations above are converted to Cream formulations by incorporation of 0.5 pts of cetyl alcohol in Gel 1 or 2 formulations by dissolving the alcohol in the glycerine at 49° C. before trituration of the gelating and cellulose gums.

EXAMPLE 12

Contraceptive Film 6.2 lbs of gelatin Type A100 is triturated with 0.5 lbs of hydroxyethylcelluose. 31 lbs of glycerine are added. Solution is mixed thoroughly to form a slurry. Add 33 lbs of CCon of Example 8 and 15 lbs of water. Warm to 40° C. Mix until gums and gelatin are completely hydrated. Solution is poured on polyethylene sheet to cast a film of about 3 mm thick to be cut for films to be used as contraceptive films after cooling.

We claim:

1. A contraceptive composition comprising as active ingredients a mixture of a) a betaine selected from the group consisting of N-alkyl-betaines, N-alkyl-sulfobetaines, N-acylbetaines, and a mixture of two or more said betaines and b) an amine oxide selected from the group consisting of alkyl-N,N-dimethylamine oxides, alkyl-N,N-dihydroxyethylamine oxides, acylamide t-amine oxides and a mixture of two or more said amine oxides and a carrier in the form of a sponge, condom, vaginal insert, contraceptive film, suppository or sustained release device.

2. A contraceptive sponge according to claim 1 comprising lauryl betaine and lauramine oxide.

3. A contraceptive sponge according to claim 1 comprising lauryl betaine, lauramine oxide, gelatin, glycerine, hydroxyethyl cellulose and water.

4. A contraceptive composition according to claim 1 comprising lauryl betaine, lauramine oxide, gelatin, glycerine, hydroxyethyl cellulose and cetyl alcohol.

5. A contraceptive suppository according to claim 1 comprising lauryl betaine, lauramine oxide, polyethylene glycol and povidone.

6. A contraceptive film according to claim 1 comprising N-alkyl-betaine, N-alkyl-amine oxide, type A gelatin, polyhydric alcohol and cellulose gum.

7. A contraceptive composition according to claim 1 wherein the betaines and the amine oxides are in a molar ratio of from 1:5 to 5:1.

8. A contraceptive composition according to claim 1 wherein the betaines and the amine oxides are in a molar ratio of about 1:1.

9. A contraceptive composition according to claim 1 further comprising acid in an amount sufficient to adjust the pH of the composition from 4–8 when measured in an aqueous solution of said betaine and amine oxide in an acceptable carrier and wherein said betaine and said amine oxide are in a molar ratio of from 1:5 to 5:1.

10. A contraceptive composition according to claim 1 wherein the betaine is selected from the group consisting of cocobetaine and lauryl betaine and the amine oxide is selected from the group consisting of cocoamine oxide and lauramine oxide.

11. A contraceptive composition comprising as active ingredients a mixture of N-alkyl-di (lower alkyl) betaines and alkyl N,N-di (lower alkyl) amine oxides, wherein the lower alkyl is $C_{1-3}$ and said betaine and said amine oxide are present in molar ratio of from 1:5 to 5:1.

12. A composition according to claim 11 where said N-alkyl-di (lower alkyl) betaine is an N-alkyl dimethyl betaine and said alkyl N-di (lower alkyl) amine oxide is an alkyl N-dimethyl amine oxide, and acid in an amount sufficient to adjust the pH of the composition from 4–8 when measured in an aqueous solution in an acceptable carrier.

13. A composition as in claim 12 wherein the acid is added in an amount sufficient to adjust the pH of the composition from 4.5–5.5.

14. A composition according to claim 12 wherein the alkyl dimethyl betaine and alkyl dimethyl amine oxides are in a molar ratio of about 1:1.

15. A composition according to claim 12 wherein the alkyl dimethyl betaine is selected from the group consisting of cocobetaine and lauryl betaine and the alkyl dimethyl amine oxide is selected from the group consisting of cocoamine oxide and lauramine oxide.

16. A douche comprising a mixture of a) a betaine selected from the group consisting of N-alkyl-betaines, N-alkylsulfobetaines, N-acyl-betaines and a mixture of two or more said betaines and b) an amine oxide selected from the group consisting of alkyl-N,N-dimethylamine oxides, alkyl-N,N-dihydroxyethylamine oxides, acylamide t-dimethylamine oxides, and a mixture of two or more amine oxides thereof and wherein said betaine and said amine oxide are in a molar in ratio of from 1:5 to 5:1.

17. A method for inhibiting the activity of sperm comprising applying to a locus where sperm are present or will come in contact with sperm a spermicidally effective amount of a composition comprising a mixture of a) a betaine selected from the group consisting of N-alkyl-betaines, N-alkyl-sulfobetaines, N-acyl-betaines and a mixture of two or more said betaines and b) an amine oxide selected from the group consisting of alkyl-N,N-dimethylamine oxides, alkyl-N,N-dihydroxyethylamine oxides, acylamide t-amine oxides and a mixture of two or more of said amine oxides.

18. A method according to claim 17 wherein the composition comprises:
   a) an alkyl dimethyl betaine;
   b) an alkyl dimethyl amine oxide and
   c) acid in an amount sufficient to adjust the pH of the composition from 4-8 when measured in an aqueous solution of components (a) and (b) in an acceptable carrier and wherein said betaine and said amine oxide are in a molar ratio of from 1:5 to 5:1.

19. A method according to claim 17 wherein the spermicide composition is incorporated into a contraceptive sponge, condom, vaginal insert, contraceptive film, suppository or sustained release device.

20. A method according to claim 17 wherein the spermicide composition is in the form of a foam, cream, jelly, gel or spray.

21. A method according to claim 17 wherein the betaines and the amine oxides are in a molar ratio of from 1:5 to 5:1.

22. A method according to claim 17 wherein the betaines and the amine oxides are in a molar ratio of about 1:1.

23. A method according to claim 17 wherein the composition is applied vaginally.

24. A method according to claim 17 wherein the composition is applied to a condom.

25. A method according to claim 17 wherein the betaine is N-alkyl-betaine.

26. A method according to claim 17 wherein the betaine is N-alkyl-sulfobetaine.

27. A method according to claim 17 wherein the betaine is N-acyl-betaine.

28. A method for inhibiting the activity of sperm comprising applying to a locus where sperm are present or will come in contact with sperm a spermicidally effective amount of a composition comprising an N-alkyl-di (lower alkyl) betaine and an alkyl N,N-di (lower alkyl) amine oxide where the lower alkyl is $C_{1-3}$ and where said betaine and said amine oxide are present in a molar ratio of from 1:5 to 5:1.

29. A method according to claim 28 where said N-alkyl-di (lower alkyl) betaine is an N-alkyl dimethyl betaine and said alkyl N,N-di (lower alkyl) amine oxide is an alkyl N-dimethyl amine oxide.

30. A method according to claim 18 wherein the alkyl dimethyl betaine and alkyl dimethyl amine oxides are in a molar ratio of about 1:1.

31. A method according to claim 18 wherein the alkyl dimethyl betaine is selected from the group consisting of cocobetaine and lauryl betaine and the alkyl dimethyl amine oxide is selected from the group consisting of cocoamine oxide and lauramine oxide.

32. A method as in claim 18 wherein the acid is added in an amount sufficient to adjust the pH of the composition from 4.5–5.5.

* * * * *